United States Patent
Fukumoto et al.

(10) Patent No.: US 10,774,109 B2
(45) Date of Patent: Sep. 15, 2020

(54) CRYSTAL OF REDUCED GLUTATHIONE AND METHOD FOR PRODUCING SAME

(71) Applicant: KYOWA HAKKO BIO CO., LTD., Tokyo (JP)

(72) Inventors: Kazunari Fukumoto, Tokyo (JP); Maya Iguchi, Tokyo (JP); Hiroshi Nagano, Tokyo (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 0 days.

(21) Appl. No.: 16/083,483

(22) PCT Filed: Mar. 10, 2017

(86) PCT No.: PCT/JP2017/009655
§ 371 (c)(1),
(2) Date: Sep. 7, 2018

(87) PCT Pub. No.: WO2017/159554
PCT Pub. Date: Sep. 21, 2017

(65) Prior Publication Data
US 2019/0085023 A1 Mar. 21, 2019

(30) Foreign Application Priority Data
Mar. 17, 2016 (JP) .................. 2016-053843

(51) Int. Cl.
| C07K 5/037 | (2006.01) |
| A61K 38/06 | (2006.01) |
| A61P 1/16 | (2006.01) |
| A61P 39/02 | (2006.01) |
| C30B 7/08 | (2006.01) |
| C30B 29/58 | (2006.01) |
| C07K 5/02 | (2006.01) |

(52) U.S. Cl.
CPC ............ *C07K 5/0215* (2013.01); *A61K 38/06* (2013.01); *C30B 7/08* (2013.01); *C30B 29/58* (2013.01)

(58) Field of Classification Search
None
See application file for complete search history.

(56) References Cited

U.S. PATENT DOCUMENTS

| 2010/0099847 A1 | 4/2010 | Shimose et al. |
| 2016/0108437 A1 | 4/2016 | Ohara et al. |

FOREIGN PATENT DOCUMENTS

| JP | 5243963 B2 | 7/2013 |
| WO | WO 2008/047792 A1 | 4/2008 |
| WO | WO 2014/192546 A1 | 12/2014 |

OTHER PUBLICATIONS

Thickness definition, the Free Dictionary, 6 pp., accessed Jan. 26, 2020, at URL thefreedictionary.com/thickness; Random House Kernerman Webster's College Dictionary definition of 2010, p. 1 of the reference (Year: 2010).*
Yamasaki et al., "Analytical Studies of polymorphism of glutathione," *Analytical Chemistry*, 18(7): 847-878 (1969).
Japanese Patent Office, International Search Report in International Patent Application No. PCT/JP2017/009655 (dated Jun. 6, 2017).
Raj, "Effect of $WO_3$ powder particle shape, size and bulk density, on the grain size and grain size distribution of tungsten metal powder," *Metal Powder Report*, 71(4): 285-287 (2016).
Yokoyama et al., "Apparatus for Measuring Flowability of Powders by Carr's Method," *Journal of the Research Association of Powder Technology, Japan*, 6(4): 28-36 (1969).
Moggach et al., "Pressure induced phase transitions in the tripeptide glutathione to 5.24 GPa: the crystal structure of glutathione-II at 2.94 GPa and glutathione-III at 3.70 GPa," *Cryst. Eng. Comm.*, 12(9): 2587-2595 (2010).
European Patent Office, Extended European Search Report in European Patent Application No. 17766554.4 (dated Sep. 30, 2019).
Japanese Patent Office, International Preliminary Report on Patentability in International Patent Application No. PCT/JP2017/009655 (dated Sep. 18, 2018).

* cited by examiner

*Primary Examiner* — Julie Ha
*Assistant Examiner* — Kristina M Hellman
(74) *Attorney, Agent, or Firm* — Leydig, Voit & Mayer, Ltd.

(57) ABSTRACT

The present invention provides a crystal of reduced glutathione having excellent powder properties and a method for producing the same. The present invention relates to a crystal of reduced glutathione, wherein the average crystal thickness is 10 μm or more.

12 Claims, 1 Drawing Sheet

CRYSTAL OF REDUCED GLUTATHIONE AND METHOD FOR PRODUCING SAME

CROSS-REFERENCE TO RELATED APPLICATIONS

This patent application is the U.S. national phase of International Patent Application No. PCT/JP2017/009655, filed Mar. 10, 2017, which claims the benefit of Japanese Patent Application No. 2016-053843, filed on Mar. 17, 2016, which are incorporated by reference in their entireties herein.

TECHNICAL FIELD

The present invention relates to a crystal of reduced glutathione having excellent powder properties and a method for producing the same.

BACKGROUND ART

Reduced glutathione (γ-L-glutamyl-L-cysteinyl-L-glycine) is a reducing compound widely existing in organisms and is known to have a detoxification effect in the liver. Therefore, reduced glutathione has been widely used as a product such as a pharmaceutical product, a health food, and a cosmetic product, or a raw material or an intermediate thereof. A crystal of reduced glutathione is known to have two types of polymorphisms: α crystal and β crystal (Non-Patent Document 1) and, a crystal which is generally utilized as a product is the α crystal because of its physical properties.

However, the α-type crystal of reduced glutathione is likely to become a needle-like or elongated columnar crystal because the crystal growth in directions other than the long-axis (longitudinal) direction is slow. The ratio of the crystal length to the crystal width becomes large because of this property, and as a result, there arises a problem that the specific volume is increased and the powder flowability is deteriorated. In order to improve the powder properties, it is necessary to allow the crystal to grow not only in the longitudinal direction, but also in the lateral direction and the height direction.

Patent Document 1 describes the improvement of the powder properties of reduced glutathione and discloses a method in which a crystal of reduced glutathione is added as a seed crystal to an aqueous solution in which reduced glutathione is dissolved, followed by stirring, thereby precipitating reduced glutathione in the aqueous solution.

RELATED ART

Patent Document

Patent Document 1: Japanese Patent No. 5243963

Non-Patent Document

Non-Patent Document 1: Yamasaki, K. et al., Analytical Chemistry, 18(7), pp. 874-878 (1969)

DISCLOSURE OF INVENTION

Problems to be Solved by the Invention

The method of Patent Document 1 is a method in which supersaturation is rapidly destroyed by adding a seed crystal to an aqueous solution containing reduced glutathione at a high concentration, and therefore has a problem that the growth of the crystal in directions other than the longitudinal direction does not catch up with, and the improvement of the powder properties is insufficient.

In view of this, an object of the present invention is to provide a crystal of reduced glutathione having excellent flowability and pulverizability, and a method for producing the same.

Means for Solving the Problems

The present invention relates to the following (1) to (10).

(1) A crystal of reduced glutathione, wherein the average crystal thickness is 10 μm or more.

(2) The crystal described in (1), wherein the ratio L/W of the average crystal length L to the average crystal width W is 6.0 or less.

(3) The crystal described in (1) or (2), wherein the loose specific volume is 2.5 mL/g or less.

(4) The crystal described in any one of (1) to (3), wherein the dense specific volume is 2.0 mL/g or less.

(5) The crystal described in any one of (1) to (4), wherein the angle of repose is 50° or less.

(6) The crystal described in any one of (1) to (5), wherein the angle of rupture is 45° or less.

(7) The crystal described in any one of (1) to (6), wherein the crystal of reduced glutathione is an α crystal.

(8) A method for producing a crystal of reduced glutathione, comprising allowing a crystal of reduced glutathione to exist in an aqueous solution containing reduced glutathione, and then adding continuously or dividedly an aqueous solution containing reduced glutathione in a supersaturated state to the aqueous solution, thereby precipitating and/or growing a crystal of reduced glutathione, and thereafter collecting the crystal of reduced glutathione contained in the aqueous solution.

(9) The production method described in (8), further comprising a step of pulverizing the collected crystal of reduced glutathione.

(10) The production method described in (8) or (9), wherein the crystal of reduced glutathione is an at crystal.

EFFECTS OF THE INVENTION

According to the present invention, a crystal of reduced glutathione having excellent flowability and pulverizability, and a method for producing the same are provided.

BRIEF DESCRIPTION OF THE DRAWINGS

In FIG. 1, the white lozenges indicate the results of the crystal of Comparative Example, and the black circles indicate the results of the crystal of Example 3.

EMBODIMENTS FOR CARRYING OUT THE INVENTION

1. Crystal of the Present Invention

Figure 2:
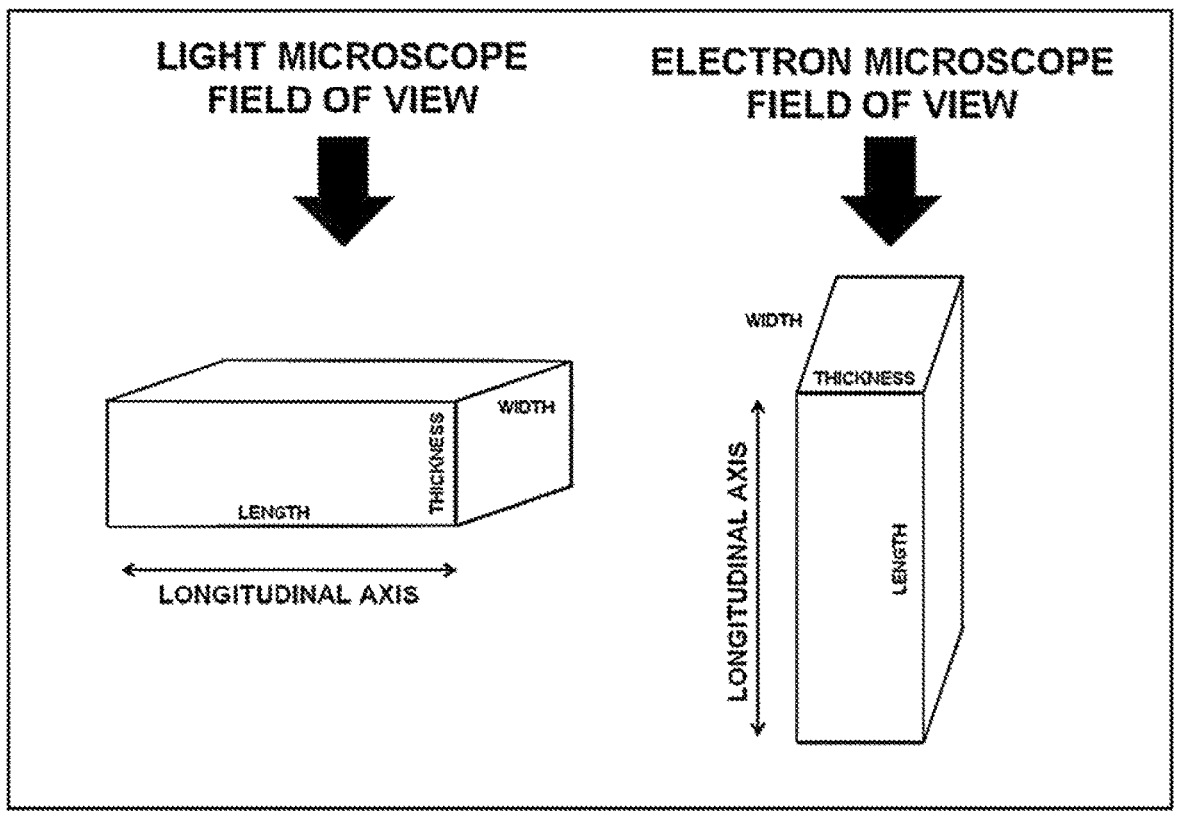
FIG. 2 illustrates a schematic view of a crystal of reduced glutathione of the present invention.

In this description, when a crystal is ascertained three-dimensionally using a microscope, the longest axis is referred to as "longitudinal axis", and an axis perpendicular to the longitudinal axis is referred to as "lateral axis" (FIG. 2). Further, the length in the longitudinal axis direction of a crystal, the major axis of the cross section of the lateral axis, and the minor axis of the cross section of the lateral axis are referred to as "crystal length", "crystal width", and "crystal thickness", respectively (see FIG. 2), and the averages thereof are referred to as "average length", "average width", and "average thickness", respectively.

Further, the average length, the average width, and the average thickness are also referred to as "L", "W", and "T", respectively. The L, W, and T can be measured by the method described in the below-mentioned Analysis Example.

The crystal length and the crystal width can be measured, for example, using a light microscope [DIGITAL MICROSCOPE VHX-900 (KEYENCE)] at a measurement magnification of 300 to 600 times. For example, the crystal length and the crystal width are measured for 200 crystals, and the average length L, the average width W, and the ratio L/W of the average length L to the average width W are calculated (FIG. 2, left drawing).

The crystal thickness can be measured, for example, using a scanning electron microscope [JSM-6510 (manufactured by JEOL Ltd.)] at a measurement magnification of 250 to 1000 times. For example, as for 50 crystals, crystals whose longitudinal axis is perpendicular to the scanning electron microscope field of view are selected, and the thickness of each crystal is measured (FIG. 2, right drawing), and the average thickness T is measured. A sample is fixed to an aluminum sample stand with a carbon double-sided tape.

The average crystal thickness (T) of the crystal of reduced glutathione of the present invention is 10 μm or more, preferably 11 μm or more, more preferably 12 μm or more, most preferably 13 μm or more.

A crystal having a large crystal thickness has excellent pulverizability, and therefore, as the crystal of reduced glutathione, a crystal having a large crystal thickness is preferred, however, as the upper limit of the average thickness of the crystal of reduced glutathione of the present invention, generally 40 μm or less, preferably 35 μm or less, more preferably 30 μm or less, most preferably 25 μm or less can be exemplified.

The ratio L/W of the average length L to the average width W of the crystal of reduced glutathione of the present invention is preferably 6.0 or less, more preferably 5.5 or less, further more preferably 5.0 or less, most preferably 4.5 or less.

A crystal having a larger L/W is a needle-like or elongated columnar crystal, and the specific volume is large, and the powder flowability is poor. Therefore, the L/W of the crystal of reduced glutathione is preferably small, however, as the lower limit of L/W, generally 1.0 or more, preferably 1.1 or more, more preferably 1.2 or more, most preferably 1.5 or more can be exemplified.

As the crystal of reduced glutathione of the present invention, a crystal of reduced glutathione in which the average crystal thickness (T) is 10 μm or more, and the L/W of the crystal is preferably 6.0 or less can be exemplified.

The loose specific volume of the crystal of reduced glutathione of the present invention is preferably 2.5 mL/g or less, more preferably 2.3 mL/g or less, further more preferably 2.2 mL/g or less, most preferably 2.0 mL/g or less.

A crystal having a small loose specific volume has an excellent filling property, and is easy to handle in various processing steps, and also its transport cost is low. Therefore, the crystal of reduced glutathione preferably has a small loose specific volume, however, as the lower limit of the loose specific volume, generally 1.0 mL/g or more, preferably 1.2 mL/g or more can be exemplified.

Here, the "loose specific volume" refers to a value which is obtained by dividing a volume occupied by a powder by a mass when the powder is filled in a container and the mass of the powder is measured. The loose specific volume can be measured, for example, using Multi Tester MT-1001T (manufactured by Seishin Enterprise Co., Ltd.) according to the accompanying manual under the following measurement conditions.

[Measurement Conditions for Loose Specific Volume]
Sieve: 1.4 mm
Spacer: 30 mm
Vibration width: 0.6 to 0.7 mm
Crystal volume: 40 mL As the crystal of reduced glutathione of the present invention, a crystal of reduced glutathione in which the average crystal thickness (T) is 10 μm or more, and the loose specific volume is preferably 2.5 mL/g or less can be exemplified.

The dense specific volume of the crystal of reduced glutathione of the present invention is preferably 2.0 mL/g or less, more preferably 1.8 mL/g or less, further more preferably 1.6 mL/g or less, most preferably 1.5 mL/g or less.

A crystal having a small dense specific volume has an excellent filling property, and also its transport cost is low. Therefore, the crystal of reduced glutathione preferably has a small dense specific volume, however, as the lower limit of the dense specific volume, generally 0.8 mL/g or more, preferably 1.0 mL/g or more can be exemplified.

Here, the "dense specific volume" refers to a value which is obtained by dividing a volume occupied by a powder by a mass when the powder is filled in a container and the mass of the powder is measured, and thereafter a given impact is applied to the container. The dense specific volume can be measured, for example, using Multi Tester MT-1001T (manufactured by Seishin Enterprise Co., Ltd.) according to the accompanying manual under the following measurement conditions.

[Measurement Conditions for Dense Specific Volume]
Tapping rate: 1 tap/sec
Number of taps: 200 taps As the crystal of reduced glutathione of the present invention, a crystal of reduced glutathione in which the average crystal thickness (T) is 10 μm or more, and the dense specific volume is preferably 2.0 mL/g or less can be exemplified.

A difference between the loose specific volume and the dense specific volume of the crystal of reduced glutathione of the present invention is preferably 1.2 mL/g or less, more preferably 1.0 mL/g or less. As the lower limit of the difference between the loose specific volume and the dense specific volume, generally 0.1 mL/g or more, preferably 0.2 mL/g or more can be exemplified. Here, the "difference between the loose specific volume and the dense specific volume" refers to a positive value when the dense specific volume is subtracted from the loose specific volume.

As the crystal of reduced glutathione of the present invention, a crystal of reduced glutathione in which the average crystal thickness (T) is 10 μm or more, the L/W of the crystal is preferably 6.0 or less, and the difference between the loose specific volume and the dense specific volume is preferably 1.2 mL/g or less can be exemplified.

The angle of repose of the crystal of reduced glutathione of the present invention is preferably 50° or less, more preferably 48° or less, further more preferably 47° or less, most preferably 45° or less.

A crystal having a large angle of repose cannot be completely discharged from the bottom of a hopper unless the angle of tilt of the bottom of the hopper is larger than the angle of repose when discharging the crystal from the hopper, and therefore, the device is limited and handling becomes complicated. Further, a crystal having a large angle of repose has poor flowability. Therefore, the crystal of reduced glutathione preferably has a small angle of repose, however, as the lower limit of the angle of repose, generally 30° or more, preferably 35° or more can be exemplified.

Here, the "angle of repose" refers to an angle formed by a horizontal plane and a generating line of a cone formed with a powder when the powder is allowed to gently fall onto the horizontal plane through a kind of a funnel. The angle of repose can be measured, for example, using Multi Tester MT-1001T (manufactured by Seishin Enterprise Co., Ltd.) according to the accompanying manual under the following measurement conditions.

[Measurement Conditions for Angle of Repose]

An angle-of-repose table is rotated without giving vibration, angles are read at three sites, and the arithmetic mean thereof is determined to be the angle of repose.

Sieve: 1.4 mm

Vibration width: 0.6 to 0.7 mm

An angle-of-repose table unit (part number: MT-1028) is used.

As the crystal of reduced glutathione of the present invention, a crystal of reduced glutathione in which the average crystal thickness (T) is 10 μm or more, and the angle of repose is preferably 50° or less can be exemplified.

The angle of rupture of the crystal of reduced glutathione of the present invention is preferably 45° or less, more preferably 43° or less, further more preferably 420 or less, most preferably 40° or less.

A crystal having a large difference between the angle of rupture and the angle of repose has high floodability and is difficult to control, and therefore, the difference between the angle of rupture and the angle of repose is preferably small, however, as the lower limit of the angle of rupture, generally 30° or more, preferably 35° or more can be exemplified.

Here, the "angle of rupture" refers to an angle formed by a horizontal plane and a generating line of a cone formed when a given impact is indirectly applied to a cone formed with a powder by allowing the powder to gently fall onto the horizontal plane through a kind of a funnel. The angle of rupture can be measured, for example, using Multi Tester MT-1001T (manufactured by Seishin Enterprise Co., Ltd.) according to the accompanying manual under the following measurement conditions.

[Measurement Conditions for Angle of Rupture]

An operation in which a weight attached to the bottom of an angle-of-repose table is slowly lifted under a tapping table and allowed to fall repeatedly for 3 times. In the same manner as the measurement method for the angle of repose described above, angles are read at three sites, and the arithmetic mean thereof is determined to be the angle of rupture.

As the crystal of reduced glutathione of the present invention, a crystal of reduced glutathione in which the average crystal thickness (T) is 10 μm or more, and the angle of rupture is preferably 45° or less can be exemplified.

The crystal of reduced glutathione of the present invention may be a crystalline powder including polymorphisms such as an α crystal and a β crystal, however, as the crystal of reduced glutathione, an α crystal is preferred. As the crystalline powder, a crystalline powder in which the ratio of the α crystal to the total reduced glutathione is generally 95% or more, preferably 97% or more, more preferably 98% or more, further more preferably 99% or more, particularly preferably 99.5% or more, most preferably 99.9% or more can be exemplified.

2. Production Method of the Present Invention

The production method of the present invention is a method comprising allowing a crystal of reduced glutathione to exist in an aqueous solution containing reduced glutathione, and then adding continuously or dividedly an aqueous solution containing reduced glutathione in a supersaturated state to the aqueous solution, thereby precipitating and/or growing a crystal of reduced glutathione, and thereafter collecting the crystal of reduced glutathione contained in the aqueous solution.

The solution containing reduced glutathione may be a solution produced by any production method of a fermentation method, an enzymatic method, an extraction method from a natural product, a chemical synthesis method, and the like. For example, a solution obtained by removing insoluble substances from a culture containing reduced glutathione obtained by culturing a microorganism having an ability to produce glutathione (WO 2008/126784), an aqueous solution containing reduced glutathione obtained by an enzymatic method [Appl. Microbiol. Biotechnol., 66, 233 (2004), JP-A-60-105499, etc.], or the like can be exemplified. More preferably, an aqueous solution of reduced glutathione obtained by the method described in Example 1 of Japanese Patent No. 5243963 can be exemplified.

As the method for allowing a crystal of reduced glutathione to exist in an aqueous solution containing reduced glutathione, for example, a method in which a crystal of reduced glutathione is crystallized in an aqueous solution containing reduced glutathione by concentrating the aqueous solution containing reduced glutathione to a concentration equal to or higher than the saturation solubility can be exemplified. When the crystal is crystallized by concentration, stirring may be performed.

The method for concentrating the aqueous solution containing reduced glutathione is not particularly limited, and for example, evaporation under reduced pressure conditions or a method using a reverse osmosis membrane can be exemplified.

As the concentration of reduced glutathione in the aqueous solution containing reduced glutathione when a crystal of reduced glutathione is crystallized, generally 100 g/L or more, preferably 250 g/L or more, more preferably 400 g/L or more can be exemplified.

Further, as the method for allowing a crystal of reduced glutathione to exist in an r aqueous solution containing reduced glutathione, for example, a method in which before a crystal of reduced glutathione is crystallized by concentrating the aqueous solution containing reduced glutathione, a crystal of reduced glutathione is added as a seed crystal so that the concentration in the aqueous solution containing reduced glutathione becomes generally 0.05 to 25 g/L, preferably 0.1 to 10 g/L, thereby crystallizing the crystal can be exemplified. When the crystal is crystallized by adding a seed crystal, stirring may be performed.

As the temperature when the crystal of reduced glutathione is crystallized, generally 0 to 50° C., preferably 5 to 40° C., more preferably 10 to 30° C. can be exemplified.

By adding continuously or dividedly an aqueous solution containing reduced glutathione in a supersaturated state to the aqueous solution in which the crystal of reduced glutathione is allowed to exist, the crystal of reduced glutathione can be precipitated and/or grown.

The "precipitating and/or growing the crystal of reduced glutathione" includes 1) newly crystallizing a crystal of reduced glutathione in the aqueous solution containing reduced glutathione, 2) enlarging the crystallized crystal, and 3) enlarging the crystal of reduced glutathione allowed to exist in the aqueous solution containing reduced glutathione before adding the aqueous solution containing reduced glutathione in a supersaturated state, by adding the aqueous solution containing reduced glutathione in a supersaturated state.

The aqueous solution containing reduced glutathione in a supersaturated state can be prepared by the same method as described above.

The temperature at which the aqueous solution containing reduced glutathione in a supersaturated state is added is not particularly limited as long as reduced glutathione is not precipitated, however, generally 0 to 50° C., preferably 5 to 40° C., more preferably 10 to 30° C. can be exemplified.

The addition of the aqueous solution containing reduced glutathione in a supersaturated state may be performed continuously at a given rate, or may be performed by dividing the total liquid amount into portions.

When the aqueous solution containing reduced glutathione in a supersaturated state is added in divided portions, the aqueous solution containing reduced glutathione in a supersaturated state can be divided into portions and added an arbitrary number of times, and the respective divided portions can be added at arbitrary intervals. Further, when the reduced glutathione-containing aqueous solution in a supersaturated state is not added, only stirring may be continued.

As the time required for adding the aqueous solution containing reduced glutathione in a supersaturated state, generally 4 to 50 hours, preferably 7 to 40 hours, more preferably 10 to 30 hours can be exemplified.

As the amount of the aqueous solution containing reduced glutathione in a supersaturated state to be added, generally 2 to 200 times equivalent, preferably 5 to 100 times equivalent, more preferably 8 to 50 times equivalent with respect to the aqueous solution containing reduced glutathione in which the crystal of reduced glutathione is crystallized can be exemplified.

By cooling after adding the reduced aqueous solution containing reduced glutathione, the precipitation and/or growth of the crystal of glutathione can be accelerated. As the cooling temperature, generally 40° C. or lower, preferably 30° C. or lower, more preferably 20° C. or lower can be exemplified.

After adding the aqueous solution containing reduced glutathione in a supersaturated state, by adding or dropping a solvent selected from the group consisting of alcohols and ketones as needed, the precipitation and/or growth of the crystal of reduced glutathione can be accelerated.

It is also possible to use a solution obtained by mixing an alcohol or a ketone with water at an arbitrary ratio in place of the solvent selected from the group consisting of alcohols and ketones.

As the alcohols, preferably C1 to C6 alcohols, more preferably C1 to C3 alcohols, further more preferably alcohols selected from the group consisting of methanol, ethanol, n-propanol, and isopropyl alcohol, most preferably alcohols selected from the group consisting of methanol and ethanol can be exemplified.

As the ketones, preferably ketones selected from acetone, methyl ethyl ketone, and diethyl ketone, more preferably acetone can be exemplified.

The temperature when the alcohols and the ketones are added or dropped may be any temperature as long as it is a temperature at which reduced glutathione is not decomposed, however, in order to improve the crystallization ratio of the crystal of reduced glutathione by decreasing the solubility, generally 40° C. or lower, preferably 30° C. or lower, more preferably 25° C. or lower, most preferably 20° C. or lower can be exemplified. As the lower limit of the temperature, generally 0° C. or higher, preferably 5° C. or higher can be exemplified.

As the amount of the alcohols and the ketones to be added or dropped, generally 0.1 to 3 times, preferably 0.2 to 2 times the amount of the aqueous solution can be exemplified.

After the crystal of reduced glutathione is precipitated and/or grown as described above, the aqueous solution containing the grown crystal is further stirred or left as such at generally 0 to 40° C., preferably 5 to 30° C., more preferably 5 to 20° C. for generally 1 to 48 hours, preferably 1 to 24 hours, most preferably 1 to 12 hours, whereby the crystal can be aged.

The "aging" refers to further growing the crystal by stopping the step of precipitating the crystal of reduced glutathione.

The aging of the crystal is performed for growing the crystal as the main purpose, however, simultaneously with the growth of the crystal, precipitation of a new crystal may occur.

After aging the crystal, the step of precipitating and/or growing the crystal of reduced glutathione may be restarted.

As the method for collecting the crystal of reduced glutathione obtained by precipitating and/or growing the crystal or the crystal from the aqueous solution containing the crystal of reduced glutathione obtained by further aging in the above, for example, collection by filtration, pressure filtration, suction filtration, centrifugation, and the like can be exemplified. Further, in order to reduce the adhesion of the mother liquor to the crystal so as to improve the quality of the crystal, after collecting the crystal, the crystal may be washed as appropriate.

A solution to be used for washing is not particularly limited, however, water, methanol, ethanol, acetone, n-propanol, isopropyl alcohol, and one type of solution selected therefrom, or a solution obtained by mixing a plurality of types selected therefrom at an arbitrary ratio can be used.

A wet crystal obtained in the above may be dried. The drying condition may be any condition as long as it is a method capable of maintaining the form of the crystal of reduced glutathione, and for example, reduced pressure drying, vacuum drying, fluidized bed drying, ventilation drying, and the like can be exemplified.

The drying temperature may be any temperature as long as adhesive water or a solution can be removed, and reduced glutathione is not decomposed, however, generally, 70° C. or lower, preferably 60° C. or lower, more preferably 50° C. or lower can be exemplified.

The crystal of reduced glutathione of the present invention can be produced by further pulverizing the crystal of reduced glutathione of the present invention obtained by the above-mentioned method. The pulverization of the crystal can be performed, for example, using Osterizer Oster Vintage Blender 16-speed Dual Range (Osterizer OSTER) under the following conditions.

[Conditions for Pulverization of Crystal]
Rotation speed: 33700 to 33900 r/min
Diameter: 50 mm
Sample feeding amount: 20 g/feed

EXAMPLES

Hereinafter, Examples will be shown, however, the present invention is not limited to the following Examples.

Example 1

Production of Crystal of the Present Invention (1)

An aqueous solution containing reduced glutathione at a concentration of 125 g/L was obtained according to the method described in Example 1 of Japanese Patent No. 5243963. The aqueous solution was concentrated to 530 g/L by heating under reduced pressure. To 180 mL of the concentrated solution at 25° C., 0.02 g of an α-type crystal of reduced glutathione (manufactured by Kojin Co., Ltd.) was added as a seed crystal, followed by stirring, whereby the α-type crystal of reduced glutathione was crystallized.

To the aqueous solution, 3850 mL of an aqueous solution containing reduced glutathione concentrated to 520 to 530 g/L was added at 25° C. over 17 hours, whereby the crystal was precipitated and/or grown. The obtained aqueous solution containing the α-type crystal of reduced glutathione was cooled to 10° C., and 0.3 times equivalent of ethanol was added thereto, and thereafter, the α-type crystal of reduced glutathione obtained by removing the aqueous solution layer through centrifugation was washed with 30 v/v % ethanol, and then dried by ventilation at 40° C., whereby the α-type crystal of reduced glutathione was obtained.

Example 2

Production of Crystal of the Present Invention (2)

An aqueous solution containing reduced glutathione obtained in the same manner as in Example 1 was concentrated to 436 g/L by heating under reduced pressure. To 330 mL of the concentrated solution at 25° C., 0.02 g of an α-type crystal of reduced glutathione (manufactured by Kojin Co., Ltd.) was added as a seed crystal, followed by stirring, whereby the α-type crystal of reduced glutathione was crystallized. To the aqueous solution, 2920 mL of a reduced glutathione aqueous solution concentrated to 420 to 430 g/L was added at 25° C. over 11 hours, whereby the crystal was precipitated and/or grown.

The obtained aqueous solution containing the α-type crystal of reduced glutathione was cooled to 10° C., and 0.3 times equivalent of ethanol was added thereto, and thereafter, the α-type crystal of reduced glutathione obtained by removing the aqueous solution layer through centrifugation was washed with 30 v/v % ethanol, and then dried by ventilation at 40° C., whereby the α-type crystal of reduced glutathione was obtained.

Example 3

Production of Crystal of the Present Invention (3)

An aqueous solution containing reduced glutathione at a concentration of 134 g/L was prepared in the same manner as in Example 1, and thereafter concentrated to 540 g/L by heating under reduced pressure. To 190 mL of the concentrated solution at 25° C., 0.02 g of an α-type crystal of glutathione (manufactured by Kojin Co., Ltd.) was added as a seed crystal, followed by stirring, whereby the α-type crystal of reduced glutathione was crystallized.

To the aqueous solution, 3920 mL of a reduced glutathione aqueous solution concentrated to 540 to 550 g/L was added at 25° C. over 15 hours, whereby the crystal was precipitated and/or grown. The obtained aqueous solution containing the α-type crystal of reduced glutathione was cooled to 10° C., and 0.3 times equivalent of ethanol was added thereto, and thereafter, the α-type crystal of reduced glutathione obtained by removing the aqueous solution layer through centrifugation was washed with 30 v/v % ethanol, and then dried under reduced pressure at room temperature using a box can, whereby the α-type crystal of reduced glutathione was obtained.

Comparative Example

An aqueous solution containing reduced glutathione at a concentration of 179 g/L was obtained according to the method described in Example 1 of Japanese Patent No. 5243963. The aqueous solution was concentrated to 546 g/L by heating under reduced pressure. To 950 mL of the concentrated solution at 25° C., 0.05 g of an α-type crystal of reduced glutathione (manufactured by Kojin Co., Ltd.) was added as a seed crystal. After the seed crystal was added, stirring was performed at 25° C. for 10 hours, whereby the α-type crystal of reduced glutathione was crystallized.

To the obtained aqueous solution containing the α-type crystal of reduced glutathione was added 0.3 times equivalent of ethanol, the mixture was cooled to 10° C. and thereafter, the α-type crystal of reduced glutathione obtained by removing the aqueous solution layer through centrifugation was washed with 60 v/v % ethanol, and then dried under reduced pressure at 40° C., whereby the α-type crystal of reduced glutathione was obtained.

Example 4

Measurement of Powder Properties

With respect to the α-type crystals of reduced glutathione obtained in Examples 1 to 3, the α-type crystal of reduced glutathione obtained in Comparative Example, and commercially available α-type crystals of reduced glutathione (commercially available products A and B), the average length L, the average width W, the ratio L/W of the average length L to the average width W, the loose specific volume, and the dense specific volume of the crystal were measured. The results are shown in Table 1.

TABLE 1

| Sample | L [μm] | W [μm] | L/W [—] | Loose specific volume [mL/g] | Dense specific volume [mL/g] | Difference in specific volume [mL/g] |
|---|---|---|---|---|---|---|
| Commercially available product A | 24 to 33 | 3 to 4 | 7 to 9 | 4.69 | 2.49 | 2.20 |
| Commercially available product B | 46 to 55 | 4 to 5 | 11 to 15 | 5.50 | 2.88 | 2.61 |
| Comparative Example | 77 to 94 | 10 to 11 | 8 to 11 | 3.42 | 1.95 | 1.48 |
| Example 1 | 75 to 80 | 27 to 29 | 2.7 to 3.2 | 1.88 | 1.26 | 0.62 |
| Example 2 | 49 to 57 | 24 to 27 | 2.0 to 2.4 | 2.00 | 1.29 | 0.71 |
| Example 3 | 67 to 95 | 23 to 26 | 2.9 to 4.1 | 2.00 | 1.29 | 0.71 |

As shown in Table 1, it was found that in the case of the crystals of the present invention obtained in Examples 1 to 3, the L/W, the loose specific volume, the dense specific volume, and the difference between the loose specific volume and the dense specific volume are all smaller, and the flowability is higher, and the powder properties are superior as compared with the crystal of glutathione obtained in Comparative Example and the commercially available products A and B.

In addition, the average crystal thickness T of each of the α-type crystals of reduced glutathione obtained in Examples 1 to 3, the α-type crystal of reduced glutathione obtained in Comparative Example, and the commercially available product A was measured. The results are shown in Table 2.

TABLE 2

| Sample | Average crystal thickness T [μm] |
|---|---|
| Commercially available product A | 1.9 |
| Comparative Example | 5.5 |
| Example 1 | 17.0 |
| Example 2 | 16.7 |
| Example 3 | 16.7 |

As shown in Table 2, it was found that in the case of the α-type crystals of reduced glutathione obtained in Examples 1 to 3, the average crystal thickness T is larger, and the pulverizability is superior as compared with the α-type crystal of reduced glutathione obtained in Comparative Example and the commercially available product A.

Example 5

Production of Crystal of the Present Invention (4)

The α-type crystals of reduced glutathione obtained in Example 3 and Comparative Example were pulverized, and the change in loose specific volume over time was measured.

Figure 1:
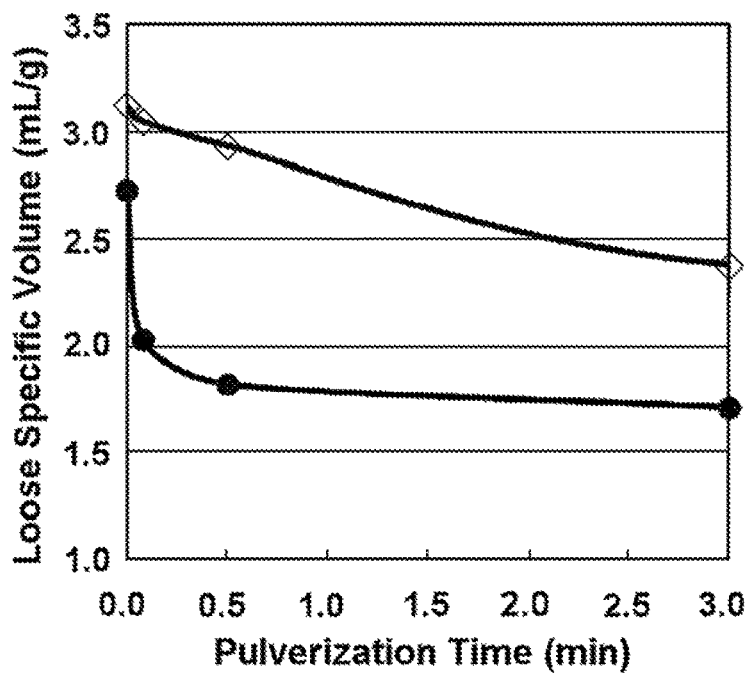
FIG. 1 illustrates the change in loose specific volume over time when crystals of reduced glutathione obtained in Example 3 and Comparative Example were pulverized. The vertical axis represents the loose specific volume (mL/g), and the horizontal axis represents the pulverization time (min).

As a result, it was found that the α-type crystal of reduced glutathione obtained in Example 3 is pulverized more promptly than the α-type crystal of reduced glutathione obtained in Comparative Example and the specific volume thereof converges to a small value (FIG. 1).

Further, the loose specific volume of the α-type crystal of reduced glutathione obtained in Example 3 was smaller than that of the α-type crystal of reduced glutathione obtained in Comparative Example in all pulverization times.

Further, with respect to the α-type crystal of reduced glutathione obtained in Example 3 and the α-type crystal of reduced glutathione obtained in Comparative Example, the angle of repose and the angle of rupture were measured. The results are shown in Table 3.

TABLE 3

| Sample | | Angle of repose [°] | Angle of rupture [°] |
|---|---|---|---|
| Comparative Example | Before pulverization | 51.4 | 46.8 |
| | After pulverization | 51.8 | 41.5 |
| Example 3 | Before pulverization | 42.4 | 39.4 |
| | After pulverization | 37.4 | 31.1 |

As shown in Table 3, it was found that in the case of the α-type crystal of reduced glutathione obtained in Example 3, the angle of repose and the angle of rupture are smaller than those of the α-type crystal of reduced glutathione obtained in Comparative Example both before and after pulverization, and therefore, the flowability is high and the powder properties are excellent.

From the above-mentioned results, it was found that the crystals of the present invention have excellent pulverizability and powder properties as compared with the currently available crystals of reduced glutathione.

While the present invention has been described in detail with reference to specific embodiments, it is apparent to those skilled in the art that various changes and modifications can be made without departing from the spirit and scope of the present invention. The present application is based on Japanese Patent Application (Japanese Patent Application No. 2016-53843) filed on Mar. 17, 2016 and the entire contents of which are incorporated herein by reference. Further, all references cited herein are incorporated herein by reference in their entirety.

INDUSTRIAL APPLICABILITY

According to the present invention, a crystal of reduced glutathione having excellent powder properties and a method for producing the same are provided.

The invention claimed is:

1. A crystal of reduced glutathione, wherein the crystal has an average crystal length, an average crystal width, and an average crystal thickness, and the average crystal thickness is smaller than the average crystal length and the average crystal width, and wherein the average crystal thickness is 10 μm to 40 μm.

2. The crystal according to claim 1, wherein the crystal has a ratio L/W of the average crystal length L to the average crystal width W of 6.0 or less.

3. The crystal according to claim 2, wherein the crystal has a loose specific volume of 1.0 mL/g to 2.5 mL/g.

4. The crystal according to claim 3, wherein the crystal has a dense specific volume of 0.8 mL/g to 2.0 mL/g.

5. The crystal according to claim 4, wherein the crystal has an angle of repose of 30° to 50°.

6. The crystal according to claim 5, wherein the crystal has an angle of rupture of 30° to 45°.

7. The crystal according to claim 6, wherein the crystal of reduced glutathione is an α crystal.

8. The crystal according to claim 1, wherein the crystal has a loose specific volume of 1.0 mL/g to 2.5 mL/g.

9. The crystal according to claim 1, wherein the crystal has a dense specific volume of 0.8 mL/g to 2.0 mL/g.

10. The crystal according to claim 1, wherein the crystal has an angle of repose of 30° to 50°.

11. The crystal according to claim 1, wherein the crystal has an angle of rupture of 30° to 45°.

12. The crystal according to claim 1, wherein the crystal of reduced glutathione is an α crystal.

* * * * *